(12) United States Patent
Herzog et al.

(10) Patent No.: US 11,819,708 B1
(45) Date of Patent: Nov. 21, 2023

(54) ROBOTIC LASER TREATMENT SAFETY SYSTEM

(71) Applicant: BellaMia Technologies, Inc., San Antonio, TX (US)

(72) Inventors: Donald G. Herzog, Collingswood, NJ (US); Edward J. Adamkiewicz, Longwood, FL (US)

(73) Assignee: BELLAMIA TECHNOLOGIES, INC., San Antonio, TX (US)

( * ) Notice: Subject to any disclaimer, the term of this patent is extended or adjusted under 35 U.S.C. 154(b) by 0 days.

(21) Appl. No.: 17/952,962

(22) Filed: Sep. 26, 2022

Related U.S. Application Data

(63) Continuation-in-part of application No. 17/854,703, filed on Jun. 30, 2022, which is a continuation-in-part of application No. 17/746,516, filed on May 17, 2022, application No. 17/952,962 is a continuation-in-part of application No. 17/746,516, filed on May 17, 2022.

(51) Int. Cl.
| | | |
|---|---|---|
| A61N 5/067 | (2006.01) |
| B25J 19/02 | (2006.01) |
| A61B 90/50 | (2016.01) |
| A61B 90/00 | (2016.01) |
| A61N 5/06 | (2006.01) |
| A61B 17/00 | (2006.01) |
| A61B 18/00 | (2006.01) |
| A61B 34/30 | (2016.01) |

(52) U.S. Cl.
CPC ............ *A61N 5/067* (2021.08); *B25J 19/022* (2013.01); *A61B 34/30* (2016.02); *A61B 2017/00057* (2013.01); *A61B 2018/00886* (2013.01); *A61B 2090/049* (2016.02); *A61B 2090/5025* (2016.02); *A61N 2005/0626* (2013.01)

(58) Field of Classification Search
CPC ............ A61N 5/067; A61N 2005/0626; B25J 19/022; A61B 34/30; A61B 2017/00057; A61B 2018/00886; A61B 2090/049; A61B 2090/5025
See application file for complete search history.

(56) References Cited

U.S. PATENT DOCUMENTS

| | | | |
|---|---|---|---|
| 8,036,448 | B2 | 10/2011 | Gildenberg |
| 9,084,622 | B2 | 7/2015 | Rastegar et al. |
| 11,065,469 | B2 | 7/2021 | Lee et al. |
| 11,103,310 | B2 | 8/2021 | Lee |

(Continued)

FOREIGN PATENT DOCUMENTS

| | | | |
|---|---|---|---|
| WO | 2017/080016 | 5/2017 | |
| WO | 2020/001466 | 1/2020 | |
| WO | WO-2021059255 A1 * | 4/2021 | ............ A61B 18/201 |

*Primary Examiner* — Gary Jackson
*Assistant Examiner* — Sebastian X Lukjan
(74) *Attorney, Agent, or Firm* — Jackson Walker LLP; Christopher J. Rourk

(57) ABSTRACT

A safety system for laser treatment, comprising a robotic controller configured to monitor a distance between a treatment device and a treatment area, the robotic controller configured to detect a manual movement of the treatment device and to generate a counterbalancing force in response to the manual movement and wherein the robotic controller is configured to increase the counterbalancing force if the distance between the treatment device and the treatment area is less than a predetermined distance.

19 Claims, 4 Drawing Sheets

(56) References Cited

U.S. PATENT DOCUMENTS

| | | | |
|---|---|---|---|
| 2006/0142657 A1* | 6/2006 | Quaid | A61B 90/37 |
| | | | 600/424 |
| 2008/0009841 A1 | 1/2008 | Kuo | |
| 2012/0071794 A1 | 3/2012 | Karni | |
| 2016/0136450 A1* | 5/2016 | Chariff | A61B 5/14532 |
| | | | 607/89 |
| 2016/0324588 A1* | 11/2016 | Durant | A61B 34/30 |
| 2019/0117308 A1* | 4/2019 | Lee | A61B 5/00 |
| 2020/0046427 A1 | 2/2020 | Hirvonen et al. | |
| 2021/0128248 A1 | 5/2021 | Cohen et al. | |
| 2021/0220667 A1 | 7/2021 | Schuster et al. | |
| 2022/0160443 A1* | 5/2022 | Spykerman | A61B 34/76 |

* cited by examiner

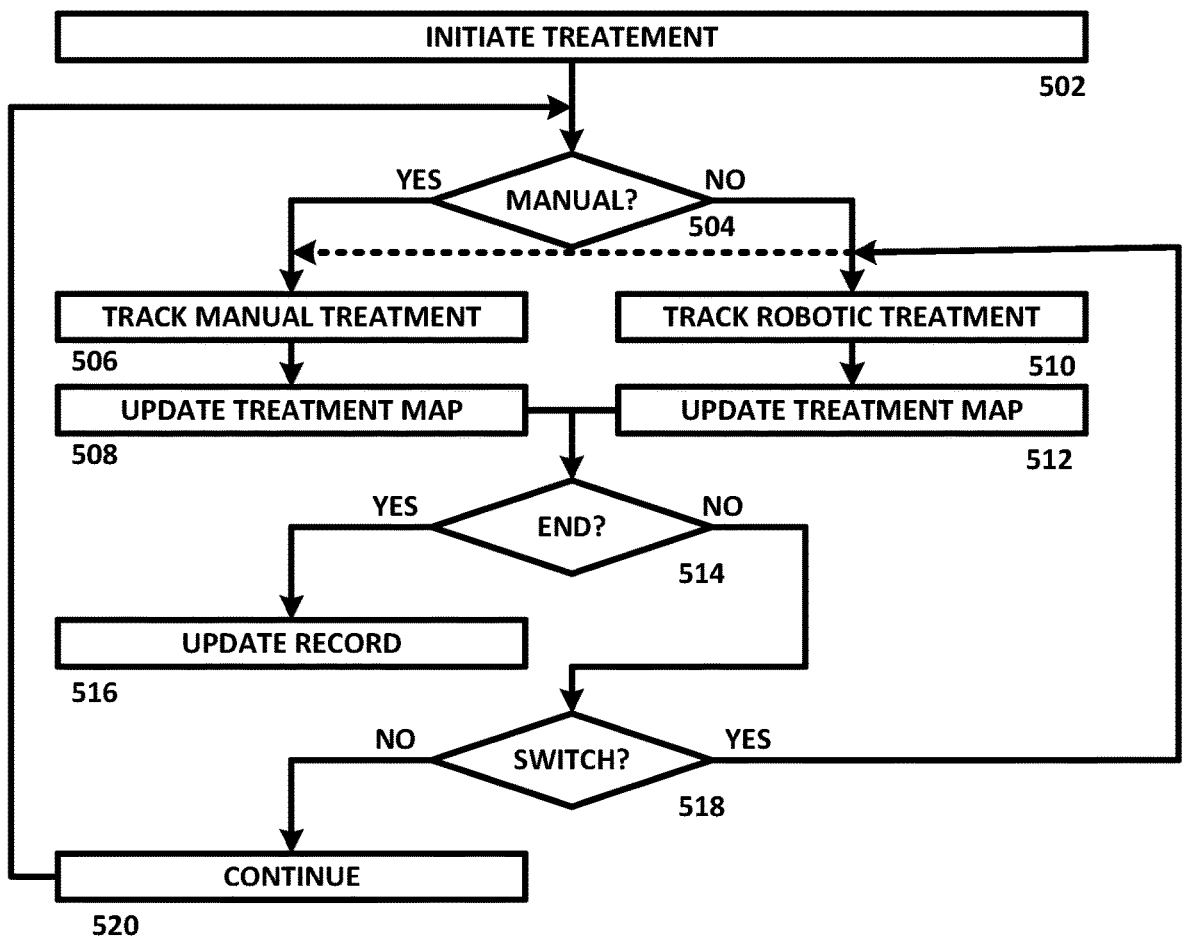

ROBOTIC LASER TREATMENT SAFETY SYSTEM

RELATED APPLICATIONS

This application is a continuation-in-part application of and claims priority to U.S. Ser. No. 17/854,703, filed Jun. 30, 2022, and U.S. Ser. No. 17/746,516, filed May 17, 2022, which are hereby incorporated by reference for all purposes as if set forth herein in their entireties.

TECHNICAL FIELD

The present disclosure relates generally to laser skin treatment, and more specifically to a robotic laser skin treatment safety system that prevents unsafe operation by a user.

BACKGROUND OF THE INVENTION

Treating skin with lasers is known, but there are many problems with existing treatment equipment that can create safety concerns.

SUMMARY OF THE INVENTION

A safety system for laser treatment is disclosed that includes a robotic controller that monitors a distance between a treatment device and a treatment area. The robotic controller detects a manual movement of the treatment device and generates a counterbalancing force in response to the manual movement. The robotic controller increases the counterbalancing force if the distance between the treatment device and the treatment area is less than a predetermined distance, such as to assist the user in regulating the distance without interfering with the treatment.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE SEVERAL VIEWS OF THE DRAWINGS

Aspects of the disclosure can be better understood with reference to the following drawings. The components in the drawings may not be to scale, but emphasis is placed upon clearly illustrating the principles of the present disclosure. Moreover, in the drawings, like reference numerals designate corresponding parts throughout the several views, and in which.

DETAILED DESCRIPTION OF THE INVENTION

Figure 1:
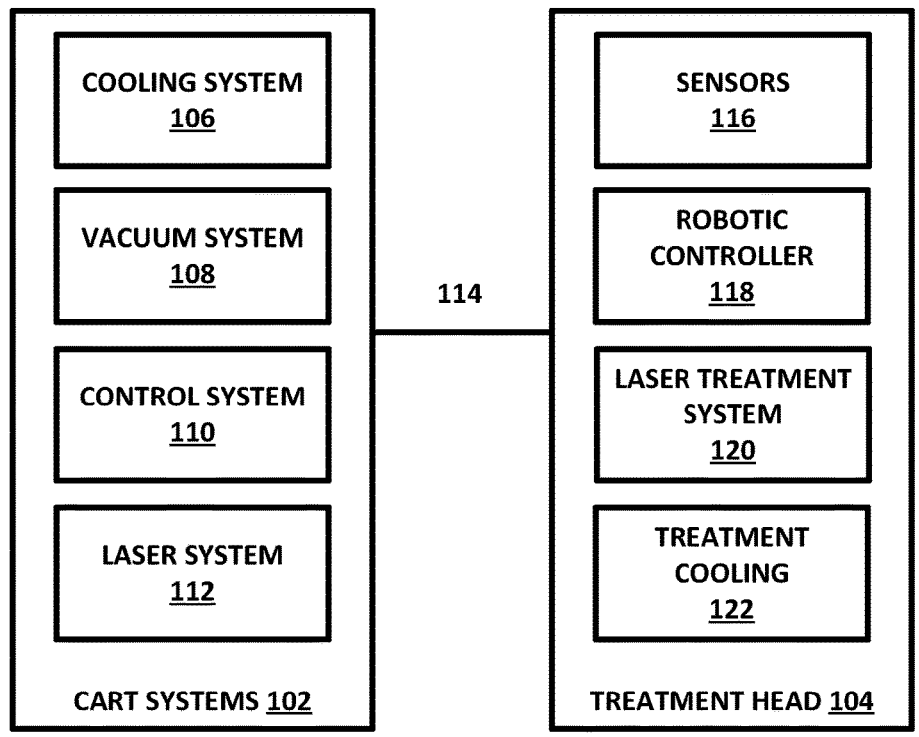
FIG. 1 is a diagram of a system for automated and manual laser skin treatment, in accordance with an example embodiment of the present disclosure.

In the description that follows, like parts are marked throughout the specification and drawings with the same reference numerals. The drawing figures may be to scale and certain components can be shown in generalized or schematic form and identified by commercial designations in the interest of clarity and conciseness.

The present disclosure provides a system and method for laser treatment of skin that addresses many problems that exist with prior art systems. The disclosure allows one or more laser wavelengths to be used simultaneously, to accelerate a final skin enhancement and improve treatment efficiency with a single system. For example, a patient may only need treatment with a single laser wavelength, but prior art systems required a practitioner to own multiple separate systems and to set up one of them for use treating the patient. With the present disclosure, the practitioner can select one or more laser wavelengths and can perform many other novel and non-obvious treatment procedures.

In one example embodiment, tabs or markings can be placed on predetermined guide locations on the patient to help register the robotics to 3D-generated images. These tabs or markings can be directed to different wavelengths, and can allow automated treatment of different areas in sequence to improve treatment time and reduce patient fatigue.

The present disclosure includes a common hand piece and function head for manual and robotic operations. In one example embodiment, the treatment head can include one or more robotic system components, so that a single hand piece can support both robotic and hand piece operations and associated treatment procedures. In this example embodiment, the robotic operations can be used for macroscopic operations such as treating large areas and the manual operations can be used for microscopic operations, such as treating areas that require fine detail procedures. Other suitable embodiments can also or alternatively be used, such as robotic system overrides that inhibit robotic system operation if movement parameters are exceeded, to prevent loss of indexing or other problems.

The present disclosure also includes the use of 3D imaging with robotics procedures. In one example embodiment, a 3D image that was generated using a laser-based 3D image generator, a multiple optical image 3D image generator or other suitable 3D image generators can be presented on the system display and one or more user controls can be generated to allow the user to rotate the image, translate the image, magnify the image and to perform other suitable processes to facilitate treatment. The manipulation of the image data can occur during manual or robotic treatment, such as to allow a practitioner to take over manual control during a robotic treatment and then to revert back to robotic control at the point where control was transferred, and where the automated treatment protocol is updated to reflect the manual treatment. In this example embodiment, areas that require treatment procedures can be identified in the 3D image data, such as by using an electronic pen or other suitable man-machine interfaces, prior to or during the treatment procedure. A footswitch or other suitable control devices can be used to toggle robot head actuation to cause the robot head to move over the skin with very exacting locations while maintaining exact separation of the head to the skin distance.

Either prior to or after a first set of robotic procedure(s) is completed, a rescan of specific areas can be outlined on the 3D image to provide additional treatment with any of the available laser wavelengths (such as one of three laser wavelengths or other suitable numbers) and/or adjustable energy or laser spot size, by using an electronic pen or other user input devices in conjunction with the 3D image. A markup of the 3D image can be generated and used to control the robotic system to perform the treatment procedure, such as by processing the markup to identify a start point, a treatment path and an end point, or in other suitable manners. Virtual markings or tabs can be created using the image data to eliminate the need for physical markings or tabs, where suitable.

Because multiple laser wavelengths can be included within the system, they can be easily and quickly switched, and multiple procedures using different wavelengths, separately or simultaneously, can be incorporated within the same robotic scan set up. This process can be accomplished by the operator using an electronic pen or other suitable user interface controls. In one example embodiment, an operator can select a laser wavelength with other laser parameters for a first treatment procedure type. Next the operator can outline the specific areas for that first treatment on the 3D image display using the user interface device. This process can be repeated for additional treatments for each laser wavelength that has been selected for a selected treatment procedure that can be done within that treatment time or later with a separate appointment time. When the robot is over a specific area that was identified and associated with a procedure and a specific wavelength, that treatment procedure can be actuated. The selected treatment procedure and laser wavelengths do not have to occur over the same outlined area of the 3D image and can be different areas, can include multiple laser treatments in the same area or other suitable processes can also or alternatively be used. The treatment procedures can be initiated, paused and terminated by pressing a footswitch or using other suitable controls.

In addition to selection of a wavelength for a treatment procedure, other parameters can also or alternatively be selected, such as an energy per pulse, a pulse width, a pulse rate, a treatment pattern, a spot size, and so forth and can be varied for selected parts of the procedure. A practitioner can interrupt a programmed robotic procedure to modify those parameters, to see whether the modifications result in an improvement, and to perform other suitable functions.

The present disclosure further includes a pause mode. In one example embodiment, when using the robotic system with a foot switch or other suitable initiated component including a display interface control or verbal command, the laser can be stopped if the foot switch goes to the off position and the robot can remain at the its last position in a pause mode. While in the pause mode, the operator can easily move the head in any direction, such as moving the head back for a rescan of the area that needs additional treatment, and because the location of the head is continuously tracked, the treatment procedures can be updated to reflect such manual treatment. This freedom to easily move the head is a unique application that can be implemented with inertial sensors, positional measurement sensors, other suitable sensors or a suitable combination of sensors. When the foot switch goes to the on position again, the robot can start the scan from a current position, its last position even though it may be a different position from when the foot switch was in the off position, or other suitable locations. When in the pause mode, the head can be easily moved to a suitable location or position, such as with the robot providing positive assist via AI to remove all resistance to the movement in all axis by the operator or in other suitable manners. It is also an option to provide a small amount of resistance to movement to give the operator the sensation of movement, to switch between a manual and robotic mode when manual movement has been detected, or to provide other suitable controls that can be initiated by operator interaction with the treatment head.

In another example embodiment, the same hand piece can be used with lasers of different wavelengths. In this example embodiment, a suitable number of laser wavelengths (such as 3 or more) can be implemented using the same hand piece, with a single cart (console) unit and with no change of hand piece with changes of procedures. When using the robotic system, different wavelength based procedures can use the same 3D image. The same hand piece can also be used when there are robotic applications. When using the robotic system, the hand piece can be described or referred to as a head. The cart (console) can support the hand piece operations, as well as the robotic operations using the same hand piece (head).

In another example embodiment, a 3D image of the treatment area is taken with a 3D image generator that accurately transcribes the treatment areas with a colored 3D image. The 3D image can be electronically transferred from the 3D image generator to the system console computer, such as using a wireline connection, a wireless connection such as a blue tooth coupling, or an equivalent approach. The computer can then provide the 3D image on the console display with controls that provide the operator with the capability of rotating and translating the image to suit the operator. The 3D image can also be magnified to provide more details of the skins surface area to the operator. The 3D image generator can be directly connected to the console via an electronic cable or in other suitable manners.

In another example embodiment, a pre-scan can be implemented prior to any treatment procedure where the robot will perform movement over the prescribed treatment area, with the lasers off. In this example embodiment, a visible beam that mimics the treatment laser can be provided to allow the operator to see the exact areas that the treatment laser beam will illuminate. Prior to the treatment, the operator can review the robot movement to confirm that the actual treatment procedure will take place as prescribed. If the pre-scan does not indicate that the intended treatment procedure will take place as prescribed, then the operator can reset or modify the procedure parameters to ensure that the proper procedure will take place in a safe manner. A repeat pre-scan will or may occur based on operator preferences.

The present disclosure allows procedure information to be stored on the system computer and retrieved at a later date, or transferred to a central computer for record keeping. The procedure data can include all image data, 3D scan data, an image of the patient to use for verifying patient identity, audiovisual data and other record data associated with the patient, such as the procedure information (energy levels, dates, time, operator, equipment and so forth). The system can be configured to store all data until removal, as part of a medical record. Data encryption and other suitable data protection mechanisms can also be used to secure the data from access by malicious actors. All or any part of the stored information regarding a particular patient can be transferred from the system via a plug in thumb drive, DVD or other suitable data storage media.

The stored information that was originally on the system or another identical system within the same facility can also be sent or retrieved from the central computer to a separate system for faster setup for a similar treatment procedure or for additional treatment of the same patient at a later date. Standard or often repeated procedures can be stored and selected from a stored list. Selected information can be transferred to the central computer system, thumb drive, DVD or other suitable data storage media using a suitable control command, such as: a) transfer all information; b) transfer patient information only; c) transfer photos, videos and images only; d) transfer procedure information only; e) transfer specific information selected from subsets of above, or transfer other suitable data. Selected information can be transferred using PDF formats only, an original stored data format, a combination of each depending on the selected information or other suitable formats.

The present disclosure can also utilize disposable shields for each patient and treatment procedure, such that the disposable shield has a unique added capability to the hand piece or head for each of the treatment procedures. In an alternative embodiment, the shields can be removable for cleaning and can then be replaced, where a cleaning procedure is specified that uses a compatible cleaning solution, UV exposure, heat exposure, or other suitable processes.

A quick disconnect can also be provided for the vacuum and cooling air connection with the disposable cover when using the 2940 nm wavelength or other suitable high power wavelengths. All other wavelengths may only need the cooling air depending on the operator and treatment procedure. The unique quick connect/disconnect technique for the disposable cover can be configured for a two finger control, to facilitate operator use, such as by including a spring loaded release, a flexible lock or other suitable mechanisms.

The disposable cover of the present disclosure for the 2940 nm wavelength or other high power wavelengths that generate plume fragments can include a HEPA filter to collect all plume fragments, where the HEPA filter can be attached to the hand piece/treatment head and can be disposed of with the disposable cover or can be cleaned and re-used. If the disposable shield is a throw-away item, it can improve the safety for the operator, patient and room environment by providing protection from contamination. When the procedure is completed, the disposable shield, including the HEPA filter (when used), can be removed and placed in an appropriate contaminated waste disposal container. The disposable cover can also protect the head and vacuum hose from damage and contamination.

The present disclosure includes a cooling air supply to the skin, which can be controlled by the amount of air, the temperature of the air or both. An infrared temperature sensor located in hand piece/treatment head can be directed at the treatment area, and a signal from the sensor can be processed to actuate an air pump, open a solenoid valve or otherwise activate the flow of cooling air.

The present disclosure anticipates that a system with a subset of the disclosed features may provide substantial utility even without a robot and associated robotic mode. In a manual-only configuration, rollers or other physical mechanisms can be used to control a separation between the laser emission point and the focus point, which will typically be located at the surface of the skin or in other suitable locations. Such rollers are not required for the robotic mode, and can be easily added or removed for mixed manual and robotic modes of operation. If the head gets too close to the skin in the robotic mode, as measured by the sensors in the head or other suitable proximity sensors and the system cannot immediately correct the error, such as by preventing movement with the robotic movement system, then the procedure can be stopped and the laser can be turned off, a warning signal to the operator can be generated or other suitable safety mechanisms can be used. The robot can then be returned to its stowed position or some designated location. When this happens, the operator can continue by resetting the treatment system using a suitable control command. The sensors can be distance measurement sensors with at least 3 individual sensors, symmetrically located around the face of the head so that the tilt of the head can be compensated for. As an alternative, a sensor could use two overlapping imaging sensors that extend beyond the procedure treatment areas and using stereoscopic data processing techniques for the distance and tilt angle can accurately measure the proximity of the head to the skin.

FIG. 1 is a diagram of a system 100 for automated and manual laser skin treatment, in accordance with an example embodiment of the present disclosure. System 100 includes cart systems 102, treatment head 104, cooling system 106, vacuum system 108, control system 110, laser system 112, connector 114, sensors 116, robot and robotic controller 118, laser treatment system 120 and treatment cooling 122, each of which can be implemented in hardware or a suitable combination of hardware and software.

Cart systems 102 can be configured to optimize space on a medical equipment cart. In one example embodiment, the cart can include power connections and distribution, data connections and distribution and other suitable physical support for providing laser treatment and supporting the associated physical requirements for patients. In this example embodiment, cart systems 102 are configured to be installed on a single cart, to optimize the space required, improve ease of handling and reduce weight and heat load.

Treatment head 104 can be configured to contain system components that are required to provide laser skin treatment in a hybrid manual/robotic device. In one example embodiment, treatment head 104 can include a grip suitable for an operator and one or more physical connections to a robotic movement system, where the robotic movement system can sense when a user is engaging the system and can respond accordingly. In this example embodiment, the robotic movement system can allow movement in three dimensions, so as to provide a seamless transition from manual control to robotic control.

Cooling system 106 is disposed in conjunction with cart systems 102, and is configured to provide cooling to the various components of cart systems 102, and with treatment head 104 over connection 114. In one example embodiment, cooling system 106 can include a heat pump, a compressor, a thermoelectric cooling system or other suitable devices for removing heat from air or hard surfaces or other suitable coolant or heat transfer media. In this example embodiment, cooling system 106 can vary a flow rate of a coolant or heat transfer media to adjust the heat removal and associated temperature of one or more targets, such as equipment or patients.

Vacuum system 108 is disposed in conjunction with cart systems 102, and is configured to provide vacuum to the various components of cart systems 102, and treatment head 104 over connection 114. In one example embodiment, vacuum system 108 can include a suction pump or other suitable devices for removing water, air or other suitable substances. In this example embodiment, vacuum system 108 can vary a suction rate to adjust the removal of water, air or substances in conjunction with a suction head, from one or more targets, such as equipment or patients. The suction head can be automatically or manually interchangeable, such as to increase or decrease a treatment area.

Control system 110 can be implemented as a special purpose processor that includes program memory and an arithmetic logic unit, a field programmable gate array, an application-specific integrated circuit or other suitable devices that are used to implement algorithmic control over the components of system 100. In one example embodiment, control system 110 can be distributed over separate processing elements of system 100, can interface with remote processing systems for data analysis or program updates, and can perform other suitable functions as discussed further herein.

Laser system 112 can include one or more solid state lasers, gas lasers, chemical lasers, excimer lasers, fiber lasers, photonic crystal lasers, semiconductor lasers, dye lasers, free-electron lasers or other suitable systems that generate laser light that is delivered to a target, such as the skin of a patient or other suitable targets. In one example embodiment, the laser light can be transmitted over fiber optic conductors through connection 114 to treatment head 104, or can be transmitted in other suitable manners.

Connector 114 is a multiple media connector that can convey cooled air transfer media (water, air), vacuum, laser energy, electrical power, instrumentation and control signals or other suitable signals or substances. In one example embodiment, connector 114 is configured to provide sufficient mechanical strength to prevent leaks or other damage, such as to isolate cooled air from vacuum lines, to prevent electrical noise and for other suitable purposes.

Sensors 116 can include 3D sensors, proximity sensors, infrared sensors, inertial sensors, treatment tracking sensors and other suitable sensors required for system 100. In one example embodiment, sensors 116 can be disposed on a patient facing surface or configured to provide data from a patient, such as where stereographic image generators, laser scanners or other types of 3D image generation are used to create a 3D map of the treatment area for a patient, where a proximity sensor is used to determine if the laser treatment head is too close to a patient's skin, where an infrared sensor is used to determine whether cooling is needed by measuring the temperature of the patient's skin, inertial sensors to determine movement of a treatment head, robotic range sensors to determine a displacement in different dimensions of a robotic actuator and other suitable sensors. Each sensor can generate analog and/or digital data in a suitable format that can be processed to determine whether a suitable control action is needed, such as actuating a cooling or vacuum system, placing a laser system in safe mode, repositioning a treatment head or for other suitable purposes.

Robot and robotic controller 118 can be implemented as a robot with one or more axes of movement and a special purpose processor that includes program memory and an arithmetic logic unit, a field programmable gate array, an application-specific integrated circuit or other suitable devices that are used to implement algorithmic control over the components of a robotic movement system. In one example embodiment, robot and robotic controller 118 can be distributed over separate processing elements of a robotic movement system, and can generate and receive data that controls or identifies movement in one or more dimensions. In one example embodiment, robot and robotic controller 118 can allow manual movement of treatment head 104, such as by tracking the manual displacement using inertial sensors, optical data, mechanical indexing devices or other suitable devices. Robot and robotic controller 118 can generate controls to create a slight positive pressure, to facilitate manual placement by preventing overshoot. Robot and robotic controller 118 can also generate movement controls by one or more steps of a stepper motor, can generate a force to prevent movement that would violate a proximity setting or in other suitable manners.

Laser treatment system 120 is configured to deliver laser light to a target, such as a skin treatment area of a patient or other suitable targets. In one example embodiment, laser treatment system can include one or more optical switching devices to redirect laser light in response to a user or robotic control, one or more focus controllers and other suitable controls.

Treatment cooling 122 is configured to deliver a cooling media such as air to treated skin, to apply vacuum to a treatment area and to perform other suitable functions. In one example embodiment, treatment cooling 122 can include a solenoid-controlled valve or other similar means for controlling a flow of cooling air, a solenoid controlled valve for controlling an amount of suction and other suitable controls.

In operation, system 100 can be used to perform manual and robotic laser treatment with multiple laser wavelengths. System 100 is configured to provide programmable treatment paths and a user interface that include 3D treatment surface data, and to allow a user to provide control indications by interfacing with the 3D treatment surface data.

Figure 2:
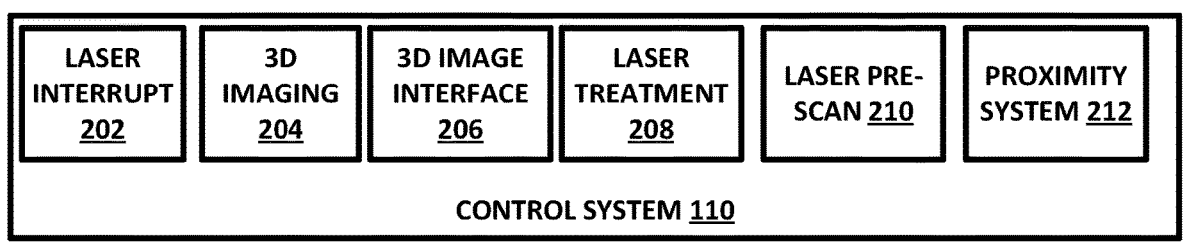
FIG. 2 is a diagram of a system for controlling a laser skin treatment system, in accordance with an example embodiment of the present disclosure.

FIG. 2 is a diagram of a system 200 for controlling a laser skin treatment system, in accordance with an example embodiment of the present disclosure. System 200 includes control system 110 and laser interrupt 202, 3D imaging 204, 3D image interface 206, laser treatment 208, laser pre-scan 210 and proximity system 212, each of which can be implemented in hardware or a suitable combination of hardware and software.

Laser interrupt 202 can be implemented as one or more algorithms that are loaded into a working memory of a processor and which cause the processor to generate control signals in response to a user control, such as a foot switch, a trigger, a voice command or other suitable user controls. In one example embodiment, laser interrupt 202 can pause an operation of a laser system, can inhibit the operation of the laser if other problems detected (such as a system misoperation or indexing error) and can perform other suitable functions.

3D imaging 204 can be implemented as one or more algorithms that are loaded into a working memory of a processor and which cause the processor to generate 3D imaging of a target treatment area. In one example embodiment, 3D imaging 204 can use stereoptic image data sets from two or more image data systems and can generate a 3D image data map as a function of differences in the image data sets. In another example embodiment, laser scanning of the treatment area can be used to generate 3D image data as a function of measured reflection data during a raster-type scan, or other suitable processes can also or alternatively be used. The 3D image data can also or alternatively include one or more tags, such as a sticker, a mark or other suitable tags that allow treatment areas to be identified, indexing to be performed or other suitable functions.

3D image interface 206 can be implemented as one or more algorithms that are loaded into a working memory of a processor and which cause the processor to generate a user interface for receiving controls and showing treatment progress. In one example embodiment, 3D image interface 206 can generate a screen display, an augmented reality display or other suitable displays that allow a user to select one or more locations or regions in the display for treatment. On the display of the 3D image, the system can also track exactly where the robotic system treatment is taking place. In this example embodiment, the display can include a user interface device such as a light pen, a touch screen or other suitable devices that allow a user to enter 3D coordinate data associated with a user-selected control, such as a laser treatment scan starting location, a laser treatment scan ending location, laser intensity selections, laser wavelength selections, laser pulse width controls or other suitable data. 3D image interface 206 can include user-readable display changes for treatment areas as they are treated, such as to show a robotic treatment progress, sections within a treatment areas that were manually treated or other suitable data.

Laser treatment 208 can be implemented as one or more algorithms that are loaded into a working memory of a processor and which cause the processor to select a laser source, to configure the laser source to have one or more user-selected parameters, and to focus the laser on a predetermined skin treatment location. In one example embodiment, a user can generate a treatment plan using 3D image interface 206, which can generate associated controls for laser treatment 208 to control the path, intensity, energy level, pulse width and other aspects of the laser treatment.

Laser pre-scan 210 can be implemented as one or more algorithms that are loaded into a working memory of a processor and which cause the processor to move a treatment head in accordance with a programmed treatment procedure prior to exposure of the area to laser light. In one example embodiment, a practitioner can generate a treatment plan and can review the treatment plan execution prior to activating the lasers, so as to ensure that the selected treatment areas are properly treated. In this example embodiment, the practitioner can interrupt the pre-scan to manually control the treatment head location and to select a learning mode where suitable, and laser pre-scan 210 can generate suitable control data to correct the treatment procedure, such as to modify start and stop locations, laser parameters or other suitable treatment parameters.

Proximity system 212 can be implemented as one or more algorithms that are loaded into a working memory of a processor and which cause the process to receive data from a proximity sensor and to detect when a laser treatment head is too close to the skin of a patient. In one example embodiment, a laser treatment plan can include a predetermined laser intensity, pulse width or other parameters that are used to control the energy that is delivered to a patient, based on an assumed distance between the laser and the patient. Data from proximity system can be generated to determine if the laser is outside of a tolerance for an ideal distance and is too close or too far away, either instantaneously or for a predetermined period of time as a function of distance, to allow corrective action to be taken.

Figure 3:
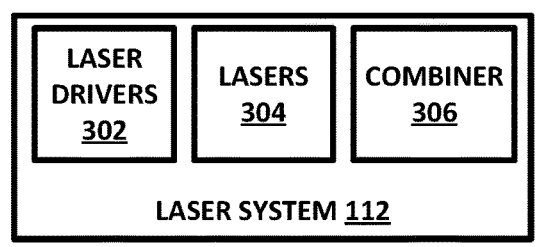
FIG. 3 is a diagram of a system for providing laser skin treatment, in accordance with an example embodiment of the present disclosure.

FIG. 3 is a diagram of a system 300 for providing laser skin treatment, in accordance with an example embodiment of the present disclosure. System 300 includes laser system 112 and laser drivers 302, lasers 304 and combiner 306, each of which can be implemented in hardware or a suitable combination of hardware and software.

Laser drivers 302 can include power amplifiers, frequency controllers and other suitable components that are used to generate a laser light signal from lasers 304, which can be solid state lasers, laser diodes, gas lasers or other suitable lasers. Lasers 304 can be configured to generate laser light at one predetermined wavelength, over a controllable pulse rate range or in other suitable manners, and can include adjustable intensity, pulse width and other suitable parameters. Combiner 306 can receive the laser light from two or more different lasers 304 and can combine the laser light into a single fiber optic or other suitable media. In one example embodiment, a multiplexer can be used to coordinate the provision of multiple laser wavelengths, such as by sequencing the pulses of each laser, by interleaving the pulses of each laser, simultaneously, or in other suitable manners.

Figure 4:
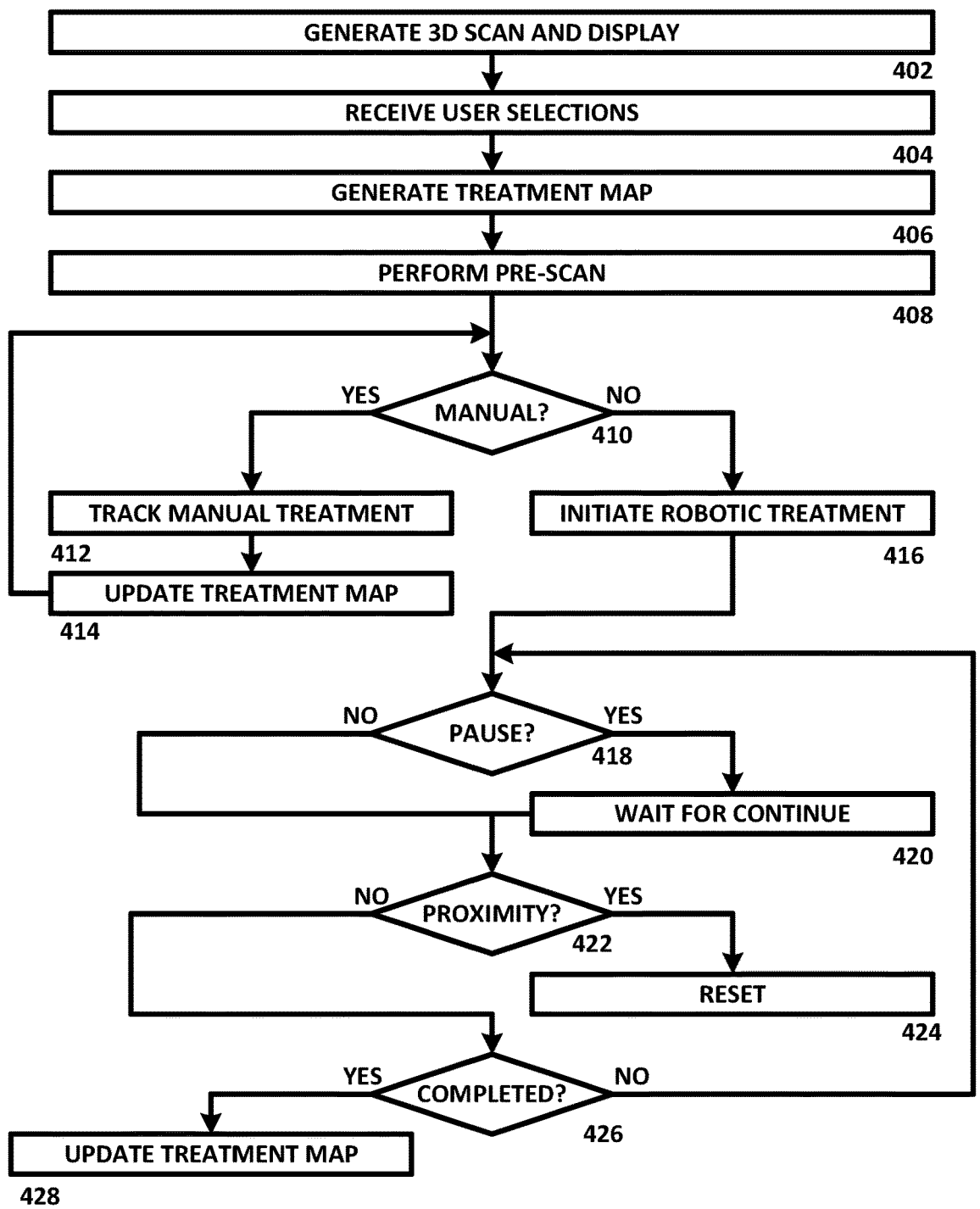
FIG. 4 is a diagram of an algorithm for controlling a laser treatment system, in accordance with an example embodiment of the present disclosure.

FIG. 4 is a diagram of an algorithm 400 for controlling a laser treatment system, in accordance with an example embodiment of the present disclosure. Algorithm 400 can be implemented on one or more processors.

Algorithm 400 begins at 402, where a 3D scan is performed of a treatment area and where a 3D display of the scanned treatment area is generated. In one example embodiment, the 3D scan can be performed automatically, after a patient has been secured in a treatment apparatus. In another example embodiment, a practitioner can move a treatment head to scan an area, and can rescan areas that do not scan clearly after an initial scan, based on the 3D display that is generated during or after scanning. The movement of the treatment head by a practitioner can be tracked using inertial sensors, optical sensors, indexing mechanisms or in other suitable manners. The algorithm then proceeds to 404.

At 404, user selections of the 3D display are received. In one example embodiment, a user interface control can be generated that prompts the user to select one or more controls, such as a laser wavelength, a start point, a stop point, a path width or other suitable data. In another example embodiment, the user can use a light pen, a stylus, a touch screen display, an augmented reality display or other suitable devices to draw a treatment area on a 3D display, to draw a treatment path or to otherwise interface with the 3D display. A grid can also or alternatively be generated on the 3D display and a user can select grid points, grid sections or other suitable display artifacts. In another example embodiment, an artificial intelligence, deep learning or other machine intelligence process can be used to identify treatment areas, such as to allow the treatment areas and results to be used to train the machine intelligence. In this example embodiment, a user control can be generated to prompt the user to select whether to use a manual treatment as training for machine learning, such as where the user determines that the manual treatment was successful or in other suitable manners. The algorithm then proceeds to 406.

At 406, a treatment map is generated. In one example embodiment, the treatment map can include the scan areas, laser settings such as wavelength, intensity, pulse width, and other suitable data, and a user can modify one or more parameters by interfacing with the treatment map or in other suitable manners. The algorithm then proceeds to 408.

At 408, a pre-scan procedure is performed. In one example embodiment, the robotic system can move the treatment head in the programmed manner, and a user interface can be generated to indicate the laser wavelengths that will be applied. If more than one laser wavelength has been selected for the procedure, then two different visible colored mimics can be used. A user control can be generated to allow a user to view parameters, interrupt the pre-scan or to take other suitable actions. The algorithm then proceeds to 404. In another example embodiment, the robotic system can be trained by the operator moving the head over the exact locations desired by a practitioner while the robotic system tracks that movement to train that procedure, or other suitable processes can also or alternatively be used. The algorithm then proceeds to 410.

At 410, it is determined whether the treatment should proceed as a manual operation or a robotic operation. In one example embodiment, the treatment can initiate as a robotic treatment and the user can use a manual control of the treatment head to switch to a manual treatment mode. If it is determined that manual treatment is being performed, the algorithm proceeds to 412, otherwise the algorithm proceeds to 416.

At 412, manual movement and treatment is tracked. In one example embodiment, the location of the treatment head can be continuously monitored and updated using inertial sensors, indexing mechanisms, optical image data, other suitable mechanisms or a combination of these mechanisms. Other suitable data can also be monitored and tracked, such as laser light selections, laser settings and so forth. The algorithm then proceeds to 414.

At 414, the treatment map is updated to reflect any changes that resulted from manual treatment. In one example embodiment, a user display can be generated and the user can be asked to confirm that the updated map reflects the treatment that was provided, and user notes can be provided to explain why the treatment was modified, for machine learning purposes or for other suitable purposes. The algorithm then returns to 410, or can alternatively proceed to 418 where suitable.

At 416, robotic treatment is initiated. In one example embodiment, robotic treatment can be a default unless a manual override has been received. The algorithm then proceeds to 418.

At 418, it is determined whether treatment should pause. In one example embodiment, a user can enter a pause control, a proximity sensor can generate a control signal, a temperature sensor can generate a control signal or other suitable data can cause the process to pause. If it is determined that a pause has not been activated, the algorithm proceeds to 422, otherwise the algorithm proceeds to 420 and awaits a continue control. In one example embodiment, the continue control can be generated by a user. Alternatively, the algorithm can enter a reset state if a proximity sensor has been actuated, or other suitable processes can also or alternatively be implemented. The algorithm then proceeds to 420.

At 422, it is determined whether a proximity control has been received. In one example embodiment, the proximity control can be configured to cause the system to reset. If it is determined that a proximity control has been received, the algorithm proceeds to 424 where a system reset is implemented. Otherwise, the algorithm proceeds to 426.

At 426, it is determined whether treatment has been completed. If treatment has not been completed, the algorithm proceeds and returns to 418. The algorithm can also return to 410 or other suitable processes. Otherwise, the algorithm proceeds to 428, where the treatment map is updated. In addition, machine learning or other suitable processes can also or alternatively be implemented.

In operation, algorithm 400 controls a treatment process for a system that uses multiple laser wavelengths and that allows a user to switch between a robotic mode of operation and a manual mode of operation, with automatic update of a 3D treatment map. While algorithm 400 is shown as a flow chart, a person of skill in the art will recognize that it can also or alternatively be implemented using object oriented programming, a state machine, a ladder diagram, other suitable programming paradigms or a suitable combination of programming paradigms.

Figure 5:
FIG. 5 is a diagram of an algorithm for switching between manual or robotic control, in accordance with an example embodiment of the present disclosure.

FIG. 5 is a diagram of an algorithm 500 for switching between manual or robotic control, in accordance with an example embodiment of the present disclosure. Algorithm 500 can be implemented on one or more processors.

Algorithm 500 begins at 502, where a treatment is initiated. In one example embodiment, the treatment can be a laser treatment of a skin condition, or other suitable processes can also or alternatively be used. The algorithm then proceeds to 504.

At 504, it is determined whether the treatment is manual or robotic. In one example embodiment, algorithm 500 can be used in an apparatus that allows a user to initiate a robotic procedure, then to switch to a manual procedure, and to switch back to the robotic procedure. In this example, all associated treatment data and mapping is continuously updated to avoid duplication of treatment. If it is determined that the treatment is manual, the algorithm proceeds to 506, otherwise the algorithm proceeds to 510.

At 506, manual treatment is tracked. In one example embodiment, a user can manually focus on specific areas that are difficult to handle robotically, such as where the artificial intelligence that would allow the robotic procedure to be performed is not sufficient. In this example embodiment, the manual processes can be used for training machine learning processes, or for other suitable purposes. The algorithm then proceeds to 508.

At 508, a treatment map is updated. In one example embodiment, the treatment map can include an initial treatment plan and additional data that tracks the treatment that was provided, to allow the user to identify differences or for other suitable purposes. The algorithm then proceeds to 514.

At 510, robotic treatment is tracked. In one example embodiment, the robotic treatment will typically not require special tracking, but variations between expected and actual measured parameters can be tracked, where suitable. The algorithm proceeds to 512.

At 512, the treatment map is updated. In one example embodiment, the treatment map can be updated as treatment proceeds, once a portion of the treatment is completed, or in other suitable manners. The algorithm then proceeds to 514.

At 514, it is determined whether the treatment has ended. For example, a treatment map can include a start point and an end point, and when the treatment reaches the end point it can be terminated. If treatment has ended, the algorithm proceeds to 516 and the record is updated. Otherwise, the algorithm proceeds to 518.

At 518, it is determined whether a switch between a manual mode and a robotic mode has occurred. In one example embodiment, a robotic movement controller can be configured to provide a resistance to a manual user if the manual user takes over the treatment and to pause the robotic procedure until the manual use has completed. During a manual operation, a slight positive pressure can be provided to assist the user to have an improved feel for movement, and a proximity control can be used to apply a greater movement restriction as the user approaches a proximity limit, to prevent potential injury to the patient. Likewise, a user control can be used to indicate when a switch has occurred or other suitable processes can also or alternatively be used. If it is determined that a switch has not occurred, the algorithm continues at 520, otherwise the algorithm switches and returns to either 506 if the switch is from robotic to manual, or to 510 if the switch is from manual to robotic.

In operation, algorithm 500 controls a treatment process for a system that uses multiple laser wavelengths and that allows a user to switch between a robotic mode of operation and a manual mode of operation, with automatic update of a 3D treatment map. While algorithm 500 is shown as a flow chart, a person of skill in the art will recognize that it can also or alternatively be implemented using object oriented programming, a state machine, a ladder diagram, other suitable programming paradigms or a suitable combination of programming paradigms.

Figure 6:
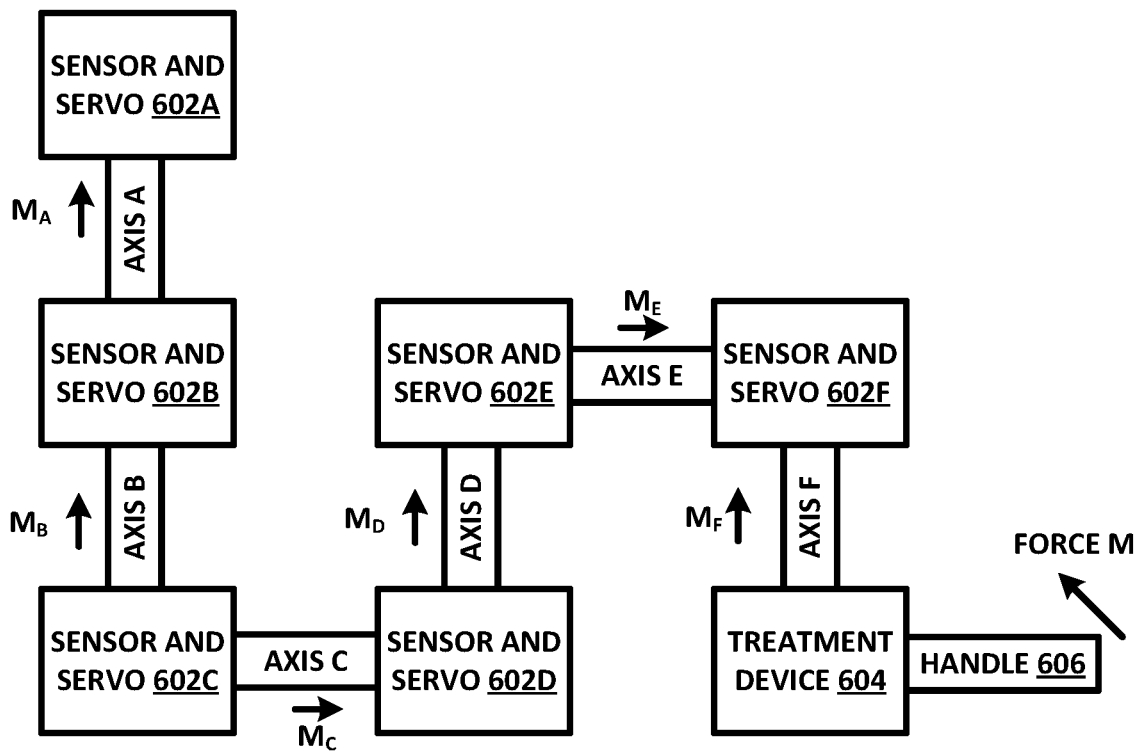
FIG. 6 is a diagram of a combined robotic and manual treatment system, in accordance with an example embodiment of the present disclosure.

FIG. 6 is a diagram of a combined robotic arm and manual treatment system 600, in accordance with an example embodiment of the present disclosure. Robotic arm and manual treatment system 600 includes sensor and servo 600A which is coupled to an associated axis A, sensor and servo 600B which is coupled to axis A and an associated axis B, sensor and servo 600C which is coupled to axis B and an associated axis C, sensor and servo 600D which is coupled to axis C and an associated axis D, sensor and servo 600E which is coupled to axis D and an associated axis E, sensor and servo 600F which is coupled to axis E and an associated axis F, treatment device 604 and handle 606, each of which can be fabricated from metal, plastic, elastomeric, other suitable materials or suitable composites of materials.

Sensors and servos 600A-F can each include one or more servo motors that are coupled to a corresponding axis A-F, respectively, and which can cause the corresponding axis to move in a predetermined manner. In one example embodiment, each of sensors and servos 600A-F can include one or more stepper motors, and can include a sensor that can detect a corresponding force component MA-MF that is a component of a manual force M that is applied by a user to handle 606. As previously discussed, sensors and servos 600A-F can operate in a first robotic mode, where force is applied in response to control signals to cause treatment device 604 to move in a predetermined manner, and can operate in a second manual mode, where a user applies a manual force M that is resolved into various force vector components along the length of a robotic arm formed by sensors and servos 600A-F and axes A-F. When a manual force is detected in robotic mode, system 600 can switch to a manual mode of operation, and can detect the force that is being applied at each of sensors and servos 600A-F through axes A-F. In the manual mode of operation, sensors and servos 600A-F and axes A-F assist the user in manual movement by generating a slight resistive force, to allow the user to gauge the amount of manual force that must be applied to move treatment device 604. In this manner, treatment device 604 can be prevented from moving too quickly, to reduce manual movement error. Sensors and servos 600A-F can detect manual movements and can use the detected manual movements to update a treatment path for treatment device 604.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

As used herein, "hardware" can include a combination of discrete components, an integrated circuit, an application-specific integrated circuit, a field programmable gate array, or other suitable hardware. As used herein, "software" can include one or more objects, agents, threads, lines of code, subroutines, separate software applications, two or more lines of code or other suitable software structures operating in two or more software applications, on one or more processors (where a processor includes one or more microcomputers or other suitable data processing units, memory devices, input-output devices, displays, data input devices such as a keyboard or a mouse, peripherals such as printers and speakers, associated drivers, control cards, power sources, network devices, docking station devices, or other suitable devices operating under control of software systems in conjunction with the processor or other devices), or other suitable software structures. In one exemplary embodiment, software can include one or more lines of code or other suitable software structures operating in a general purpose software application, such as an operating system, and one or more lines of code or other suitable software structures operating in a specific purpose software application. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections. The term "data" can refer to a suitable structure for using, conveying or storing data, such as a data field, a data buffer, a data message having the data value and sender/receiver address data, a control message having the data value and one or more operators that cause the receiving system or component to perform a function using the data, or other suitable hardware or software components for the electronic processing of data.

In general, a software system is a system that operates on a processor to perform predetermined functions in response to predetermined data fields. A software system is typically created as an algorithmic source code by a human programmer, and the source code algorithm is then compiled into a machine language algorithm with the source code algorithm functions, and linked to the specific input/output devices, dynamic link libraries and other specific hardware and software components of a processor, which converts the processor from a general purpose processor into a specific purpose processor. This well-known process for implementing an algorithm using a processor should require no explanation for one of even rudimentary skill in the art. For example, a system can be defined by the function it performs and the data fields that it performs the function on. As used herein, a NAME system, where NAME is typically the name of the general function that is performed by the system, refers to a software system that is configured to operate on a processor and to perform the disclosed function on the disclosed data fields. A system can receive one or more data inputs, such as data fields, user-entered data, control data in response to a user prompt or other suitable data, and can determine an action to take based on an algorithm, such as to proceed to a next algorithmic step if data is received, to repeat a prompt if data is not received, to perform a mathematical operation on two data fields, to sort or display data fields or to perform other suitable well-known algorithmic functions. Unless a specific algorithm is disclosed, then any suitable algorithm that would be known to one of skill in the art for performing the function using the associated data fields is contemplated as falling within the scope of the disclosure. For example, a message system that generates a message that includes a sender address field, a recipient address field and a message field would encompass software operating on a processor that can obtain the sender address field, recipient address field and message field from a suitable system or device of the processor, such as a buffer device or buffer system, can assemble the sender address field, recipient address field and message field into a suitable electronic message format (such as an electronic mail message, a TCP/IP message or any other suitable message format that has a sender address field, a recipient address field and message field), and can transmit the electronic message using electronic messaging systems and devices of the processor over a communications medium, such as a network. One of ordinary skill in the art would be able to provide the specific coding for a specific application based on the foregoing disclosure, which is intended to set forth exemplary embodiments of the present disclosure, and not to provide a tutorial for someone having less than ordinary skill in the art, such as someone who is unfamiliar with programming or processors in a suitable programming language. A specific algorithm for performing a function can be provided in a flow chart form or in other suitable formats, where the data fields and associated functions can be set forth in an exemplary order of operations, where the order can be rearranged as suitable and is not intended to be limiting unless explicitly stated to be limiting.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

What is claimed is:

1. A safety system for laser treatment, comprising:
   a treatment device disposed on a robotic arm having a plurality of force sensors;
   a treatment head disposed on the treatment device and further comprising a plurality of proximity sensors that are each configured to generate proximity data to a treatment area of a patient;
   a robotic controller configured to monitor a distance between the treatment device and the treatment area;
   the robotic controller configured to detect a manual movement of the treatment device and to generate a counterbalancing force in response to the manual movement, the proximity data and a force vector derived from the plurality of force sensors; and
   wherein the robotic controller is configured to increase the counterbalancing force if the distance between the treatment device and the treatment area is outside of a tolerance of predetermined distance.

2. The safety system of claim 1 wherein the robotic controller is configured to apply a force to decrease the distance between the treatment device and the treatment area in response to the force vector.

3. The safety system of claim 1 further comprising a laser controller configured to interrupt a laser treatment if a distance to the treatment area determined by the proximity sensors exceeds a predetermined distance.

4. The safety system of claim 1 wherein the robotic controller is configured to monitor the distance using the proximity sensors and the proximity sensors comprise an optical distance measurement device.

5. The safety system of claim 1 wherein the robotic controller is configured to apply a force to counteract the force vector and increase the distance between the treatment device and the treatment area.

6. The safety system of claim 1 further comprising a laser controller configured to detect an indexing error to interrupt a laser treatment if the treatment device is placed over the treatment area after it has been treated previously.

7. The safety system of claim 1 further comprising a laser controller configured to detect an indexing error to interrupt the laser treatment if the distance between the treatment device and the treatment area is less than the predetermined distance for a predetermined time.

8. The safety system of claim 7 wherein the laser controller is configured to continue the laser treatment upon receipt of a reset signal.

9. The safety system of claim 7 wherein the laser controller is configured to continue the laser treatment when the distance between the treatment device and the treatment area is greater than the predetermined distance.

10. The safety system of claim 1 further comprising a laser controller configured to provide an operator warning if a dwell time over the treatment area exceeds a predetermined dwell time.

11. A method for laser treatment, comprising:
    monitoring a distance between a treatment device disposed on a robotic arm having a plurality of force sensors and a treatment area using a robotic controller;
    detecting a manual movement of the treatment device using the robotic controller;
    generating a counterbalancing force in response to the manual movement and a force vector derived from the plurality of force sensors using the robotic controller; and
    increasing the counterbalancing force using the robotic controller if the distance between the treatment device and the treatment area is less than a predetermined distance.

12. The method of claim 11 further comprising applying a force to counteract the force vector to decrease the distance between the treatment device and the treatment area using the robotic controller.

13. The method of claim 11 further interrupting a laser treatment if a dwell time over the treatment area exceeds a predetermined dwell time.

14. The method of claim 11 further comprising monitoring the distance using an optical distance measurement device.

15. The method of claim 11 wherein further comprising applying a force to increase the distance between the treatment device and the treatment area in response to a manually-applied force vector.

16. The method of claim 11 further comprising interrupting a laser treatment if the treatment device is placed over the treatment area after it has been treated previously.

17. The method of claim 11 further comprising interrupting the laser treatment if the distance between the treatment device and the treatment area is less than the predetermined distance.

18. The method of claim 11 further comprising continuing the laser treatment upon receipt of a reset signal.

19. The method of claim 11 further comprising continuing the laser treatment when the distance between the treatment device and the treatment area is greater than the predetermined distance.

* * * * *